(12) United States Patent
Carlson et al.

(10) Patent No.: US 9,414,937 B2
(45) Date of Patent: *Aug. 16, 2016

(54) BONE STABILIZATION MEMBER WITH BONE SCREW RETENTION MECHANISM

(71) Applicant: Zimmer Spine, Inc., Minneapolis, MN (US)

(72) Inventors: Daniel A. Carlson, St. Louis Park, MN (US); Gregory A. Mednikov, St. Louis Park, MN (US); Eric W. Morris, Minneapolis, MN (US)

(73) Assignee: Zimmer Spine, Inc., Edina, MN (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/332,851

(22) Filed: Jul. 16, 2014

(65) Prior Publication Data

US 2014/0330385 A1  Nov. 6, 2014

Related U.S. Application Data

(63) Continuation of application No. 13/560,598, filed on Jul. 27, 2012, now Pat. No. 8,814,912.

(51) Int. Cl.
*A61B 17/88* (2006.01)
*A61F 2/44* (2006.01)
(Continued)

(52) U.S. Cl.
CPC ............ *A61F 2/447* (2013.01); *A61B 17/8042* (2013.01); *A61B 17/8052* (2013.01);
(Continued)

(58) Field of Classification Search
CPC ........... A61B 17/7044; A61B 17/8042; A61B 17/8052; A61F 2002/2835; A61F 2002/30383; A61F 2002/30397; A61F 2002/30509; A61F 2002/30828; A61F 2310/00017; A61F 2310/00023
USPC ................ 606/246–249, 264–278, 280–299; 623/17.11–17.16
See application file for complete search history.

(56) References Cited

U.S. PATENT DOCUMENTS 4,714,469 A  12/1987  Kenna et al.
4,743,256 A   5/1988  Brantigan et al.
(Continued)

FOREIGN PATENT DOCUMENTS

GB  2 457 673 A  8/2009
WO  9956653 A1  11/1999
(Continued)

*Primary Examiner* — Mary Hoffman
*Assistant Examiner* — Tara R Carter
(74) *Attorney, Agent, or Firm* — Schwegman Lundberg & Woessner, P.A.

(57) ABSTRACT

A spinal implant for stabilizing first and second vertebrae. The spinal implant includes an intervertebral spacer and a bone stabilization member configured to be coupled to the intervertebral spacer. The bone stabilization member includes a plurality of bone screw openings and a plurality of bone screws extendable through the bone screw openings to secure the bone stabilization member to the vertebrae. A retention member, which is slidably coupled to the bone stabilization member, is linearly slidable between a first position and a second position while coupled to the bone stabilization member. In the first position, each of the bone screws is permitted to be inserted into the bone screw openings, and in the second position the retention member at least partially covers each of the bone screw openings to prevent a bone screw from backing out of the respective bone screw opening.

14 Claims, 14 Drawing Sheets

(51) Int. Cl.
  *A61B 17/80* (2006.01)
  *A61F 2/28* (2006.01)
  *A61F 2/30* (2006.01)

(52) U.S. Cl.
  CPC .. *A61F 2002/2835* (2013.01); *A61F 2002/304*
    (2013.01); *A61F 2002/30383* (2013.01); *A61F*
      *2002/30397* (2013.01); *A61F 2002/30401*
    (2013.01); *A61F 2002/30504* (2013.01); *A61F*
      *2002/30578* (2013.01); *A61F 2002/30774*
    (2013.01); *A61F 2002/30787* (2013.01); *A61F*
      *2002/30828* (2013.01); *A61F 2310/00017*
      (2013.01); *A61F 2310/00023* (2013.01)

(56) References Cited

U.S. PATENT DOCUMENTS

| | | | |
|---|---|---|---|
| 4,904,261 A | 2/1990 | Dove et al. | |
| 4,955,908 A | 9/1990 | Frey et al. | |
| 5,171,278 A | 12/1992 | Pisharodi et al. | |
| 5,258,031 A | 11/1993 | Salib et al. | |
| 5,390,683 A | 2/1995 | Pisharodi et al. | |
| 5,397,364 A | 3/1995 | Kozak et al. | |
| 5,554,191 A | 9/1996 | Lahille et al. | |
| 5,571,109 A | 11/1996 | Bertagnoli | |
| 5,609,635 A | 3/1997 | Michelson | |
| 5,658,335 A | 8/1997 | Allen et al. | |
| 5,683,394 A | 11/1997 | Rinner et al. | |
| 5,713,899 A | 2/1998 | Marnay et al. | |
| 5,800,547 A | 9/1998 | Schaefer et al. | |
| 5,800,550 A | 9/1998 | Sertich et al. | |
| 5,888,223 A | 3/1999 | Bray et al. | |
| 5,951,558 A * | 9/1999 | Fiz ................ | A61B 17/8042 606/291 |
| 5,976,139 A | 11/1999 | Bramlet | |
| 6,066,175 A | 5/2000 | Henderson et al. | |
| 6,077,264 A | 6/2000 | Chemello et al. | |
| 6,096,080 A | 8/2000 | Nicholson et al. | |
| 6,099,531 A | 8/2000 | Bonutti | |
| 6,113,638 A | 9/2000 | Williams et al. | |
| 6,120,503 A | 9/2000 | Michelson et al. | |
| 6,156,037 A | 12/2000 | LeHuec et al. | |
| 6,179,873 B1 | 1/2001 | Zientek | |
| 6,183,474 B1 | 2/2001 | Bramlet et al. | |
| 6,190,413 B1 | 2/2001 | Sutcliffe | |
| 6,193,721 B1 | 2/2001 | Michelson | |
| 6,231,610 B1 | 5/2001 | Geisler | |
| 6,235,059 B1 | 5/2001 | Benezech et al. | |
| 6,241,769 B1 | 6/2001 | Nicholson et al. | |
| 6,306,136 B1 | 10/2001 | Baccelli | |
| 6,371,989 B1 | 4/2002 | Chauvin et al. | |
| 6,432,106 B1 | 8/2002 | Fraser | |
| 6,443,954 B1 | 9/2002 | Bramlet et al. | |
| 6,447,546 B1 | 9/2002 | Bramlet et al. | |
| 6,454,771 B1 | 9/2002 | Michelson | |
| 6,461,359 B1 | 10/2002 | Tribus et al. | |
| 6,468,309 B1 | 10/2002 | Lieberman | |
| 6,471,724 B2 | 10/2002 | Zdeblick et al. | |
| 6,482,233 B1 | 11/2002 | Aebi et al. | |
| 6,500,205 B1 | 12/2002 | Michelson | |
| 6,503,250 B2 | 1/2003 | Paul | |
| 6,533,786 B1 | 3/2003 | Needham et al. | |
| 6,558,423 B1 | 5/2003 | Michelson | |
| 6,579,290 B1 | 6/2003 | Hardcastle et al. | |
| 6,602,255 B1 | 8/2003 | Campbell et al. | |
| 6,610,093 B1 | 8/2003 | Pisharodi | |
| 6,626,907 B2 | 9/2003 | Campbell et al. | |
| 6,629,998 B1 | 10/2003 | Lin | |
| 6,652,525 B1 | 11/2003 | Assaker et al. | |
| 6,652,584 B2 | 11/2003 | Michelson | |
| 6,695,846 B2 | 2/2004 | Richelsoph et al. | |
| 6,695,851 B2 | 2/2004 | Zdeblick et al. | |
| 6,716,245 B2 | 4/2004 | Pasquet et al. | |
| 6,716,247 B2 | 4/2004 | Michelson | |
| 6,723,126 B1 | 4/2004 | Berry | |
| 6,730,127 B2 | 5/2004 | Michelson | |
| 6,740,088 B1 | 5/2004 | Kozak et al. | |
| 6,743,256 B2 | 6/2004 | Mason | |
| 6,770,096 B2 | 8/2004 | Bolger et al. | |
| 6,793,679 B2 | 9/2004 | Michelson | |
| 6,800,093 B2 | 10/2004 | Nicholson et al. | |
| 6,805,714 B2 | 10/2004 | Sutcliffe | |
| 6,808,537 B2 | 10/2004 | Michelson | |
| 6,824,564 B2 | 11/2004 | Crozet | |
| 6,837,905 B1 | 1/2005 | Lieberman | |
| 6,855,168 B2 | 2/2005 | Crozet | |
| 6,884,242 B2 | 4/2005 | LeHuec et al. | |
| 6,890,355 B2 | 5/2005 | Michelson | |
| 6,916,320 B2 | 7/2005 | Michelson | |
| 6,945,973 B2 | 9/2005 | Bray | |
| 6,955,691 B2 | 10/2005 | Chae et al. | |
| 6,962,606 B2 | 11/2005 | Michelson | |
| 6,972,019 B2 | 12/2005 | Michelson | |
| 6,974,479 B2 | 12/2005 | Trieu | |
| 6,984,234 B2 | 1/2006 | Bray | |
| 7,001,387 B2 | 2/2006 | Farris et al. | |
| 7,004,944 B2 | 2/2006 | Gause | |
| 7,008,453 B1 | 3/2006 | Michelson | |
| 7,018,414 B2 | 3/2006 | Brau et al. | |
| 7,033,394 B2 | 4/2006 | Michelson | |
| 7,041,135 B2 | 5/2006 | Michelson | |
| 7,044,952 B2 | 5/2006 | Michelson | |
| 7,056,341 B2 | 6/2006 | Crozet | |
| 7,060,067 B2 | 6/2006 | Needham et al. | |
| 7,070,598 B2 | 7/2006 | Lim et al. | |
| 7,077,864 B2 | 7/2006 | Byrd, III et al. | |
| 7,087,243 B2 | 8/2006 | Edgren et al. | |
| 7,112,222 B2 | 9/2006 | Fraser et al. | |
| 7,115,130 B2 | 10/2006 | Michelson | |
| 7,118,598 B2 | 10/2006 | Michelson | |
| 7,135,024 B2 | 11/2006 | Cook et al. | |
| 7,163,560 B2 | 1/2007 | Mason | |
| 7,163,561 B2 * | 1/2007 | Michelson ............ | A61F 2/442 606/307 |
| 7,166,110 B2 | 1/2007 | Yundt | |
| 7,172,627 B2 | 2/2007 | Fiere et al. | |
| 7,182,782 B2 | 2/2007 | Kirschman | |
| 7,214,243 B2 | 5/2007 | Taylor | |
| 7,217,293 B2 | 5/2007 | Branch, Jr. | |
| 7,232,464 B2 | 6/2007 | Mathieu et al. | |
| 7,291,170 B2 | 11/2007 | Huppert | |
| 7,297,162 B2 | 11/2007 | Mujwid | |
| 7,309,340 B2 | 12/2007 | Fallin et al. | |
| 7,326,248 B2 | 2/2008 | Michelson | |
| 7,326,251 B2 | 2/2008 | McCombe et al. | |
| 7,338,525 B2 | 3/2008 | Ferree | |
| 7,442,209 B2 | 10/2008 | Michelson | |
| 7,481,829 B2 | 1/2009 | Baynham et al. | |
| 7,540,882 B2 | 6/2009 | Michelson | |
| 7,594,931 B2 | 9/2009 | Louis et al. | |
| 7,618,456 B2 | 11/2009 | Mathieu et al. | |
| 7,621,943 B2 | 11/2009 | Michelson | |
| 7,641,701 B2 | 1/2010 | Kirschman | |
| 7,662,174 B2 | 2/2010 | Doubler et al. | |
| 7,662,182 B2 | 2/2010 | Zubok et al. | |
| 7,666,185 B2 | 2/2010 | Ryan et al. | |
| 7,674,279 B2 | 3/2010 | Johnson | |
| 7,704,250 B2 | 4/2010 | Michelson | |
| 7,704,255 B2 | 4/2010 | Michelson | |
| 7,704,279 B2 | 4/2010 | Moskowitz et al. | |
| 7,736,380 B2 | 6/2010 | Johnston et al. | |
| 7,758,616 B2 | 7/2010 | LeHuec et al. | |
| 7,794,502 B2 | 9/2010 | Michelson | |
| 7,833,226 B2 | 11/2010 | Grabowski et al. | |
| 7,846,188 B2 | 12/2010 | Moskowitz et al. | |
| 7,846,207 B2 | 12/2010 | Lechmann et al. | |
| 7,850,731 B2 | 12/2010 | Brittan et al. | |
| 7,862,616 B2 | 1/2011 | Lechmann et al. | |
| 7,875,076 B2 | 1/2011 | Mathieu et al. | |
| 7,887,591 B2 | 2/2011 | Aebi et al. | |
| 7,887,595 B1 | 2/2011 | Pimenta | |
| 7,892,261 B2 | 2/2011 | Bonutti | |
| 7,909,859 B2 | 3/2011 | Mosca et al. | |
| 7,942,903 B2 | 5/2011 | Moskowitz et al. | |

(56) References Cited

U.S. PATENT DOCUMENTS

| | | | |
|---|---|---|---|
| 7,972,366 B2 | 7/2011 | Richelsoph et al. | |
| 7,985,255 B2 * | 7/2011 | Bray | A61B 17/7059 623/17.11 |
| 8,016,863 B2 | 9/2011 | Kozak et al. | |
| 8,016,864 B2 | 9/2011 | Assaker et al. | |
| 8,048,075 B2 | 11/2011 | Michelson | |
| 8,048,076 B2 | 11/2011 | Michelson | |
| 8,062,294 B2 | 11/2011 | Reynolds | |
| 8,062,367 B2 | 11/2011 | Kirschman | |
| 8,114,162 B1 | 2/2012 | Bradley | |
| 8,167,919 B2 | 5/2012 | Foley et al. | |
| 8,167,946 B2 | 5/2012 | Michelson | |
| 8,211,154 B2 | 7/2012 | Fisher et al. | |
| 2001/0034553 A1 | 10/2001 | Michelson | |
| 2002/0052656 A1 | 5/2002 | Michelson | |
| 2002/0072801 A1 | 6/2002 | Michelson | |
| 2002/0116066 A1 | 8/2002 | Chauvin et al. | |
| 2002/0128717 A1 | 9/2002 | Alfaro et al. | |
| 2002/0143399 A1 | 10/2002 | Sutcliffe | |
| 2002/0193880 A1 | 12/2002 | Fraser | |
| 2003/0050701 A1 | 3/2003 | Michelson | |
| 2003/0060825 A1 | 3/2003 | Alfaro et al. | |
| 2003/0195632 A1 | 10/2003 | Foley et al. | |
| 2003/0199983 A1 | 10/2003 | Michelson | |
| 2003/0208275 A1 | 11/2003 | Michelson | |
| 2004/0078078 A1 | 4/2004 | Shepard | |
| 2004/0210310 A1 | 10/2004 | Trieu | |
| 2004/0254644 A1 | 12/2004 | Taylor | |
| 2005/0049590 A1 | 3/2005 | Alleyne et al. | |
| 2005/0071010 A1 | 3/2005 | Crozet | |
| 2005/0177236 A1 | 8/2005 | Mathieu et al. | |
| 2005/0273168 A1 | 12/2005 | Crozet | |
| 2006/0030851 A1 | 2/2006 | Bray et al. | |
| 2006/0173543 A1 | 8/2006 | Brau et al. | |
| 2006/0206208 A1 | 9/2006 | Michelson | |
| 2006/0241621 A1 | 10/2006 | Moskowitz et al. | |
| 2006/0247770 A1 | 11/2006 | Peterman | |
| 2007/0049943 A1 | 3/2007 | Moskowitz et al. | |
| 2007/0106384 A1 | 5/2007 | Bray et al. | |
| 2007/0106388 A1 | 5/2007 | Michelson | |
| 2007/0219635 A1 | 9/2007 | Mathieu et al. | |
| 2007/0233253 A1 | 10/2007 | Bray et al. | |
| 2007/0250167 A1 | 10/2007 | Bray et al. | |
| 2007/0276377 A1 | 11/2007 | Yundt | |
| 2008/0119933 A1 | 5/2008 | Aebi et al. | |
| 2008/0177307 A1 | 7/2008 | Moskowitz et al. | |
| 2008/0249625 A1 | 10/2008 | Waugh et al. | |
| 2008/0306596 A1 | 12/2008 | Jones et al. | |
| 2009/0030520 A1 | 1/2009 | Biedermann et al. | |
| 2009/0076613 A1 | 3/2009 | Biedermann et al. | |
| 2009/0080997 A1 | 3/2009 | Johnson | |
| 2009/0105830 A1 | 4/2009 | Jones et al. | |
| 2009/0182430 A1 | 7/2009 | Tyber et al. | |
| 2009/0187247 A1 | 7/2009 | Metcalf, Jr. et al. | |
| 2009/0192613 A1 | 7/2009 | Wing et al. | |
| 2009/0192615 A1 | 7/2009 | Tyber et al. | |
| 2009/0210062 A1 | 8/2009 | Thalgott et al. | |
| 2009/0210064 A1 | 8/2009 | Lechmann et al. | |
| 2009/0224023 A1 | 9/2009 | Moskowitz et al. | |
| 2009/0234455 A1 | 9/2009 | Moskowitz et al. | |
| 2010/0042167 A1 * | 2/2010 | Nebosky | A61B 17/7061 606/315 |
| 2010/0057206 A1 | 3/2010 | Duffield et al. | |
| 2010/0106249 A1 | 4/2010 | Tyber et al. | |
| 2010/0137988 A1 | 6/2010 | Markworth et al. | |
| 2010/0137989 A1 | 6/2010 | Armstrong et al. | |
| 2010/0145459 A1 | 6/2010 | McDonough et al. | |
| 2010/0145460 A1 | 6/2010 | McDonough et al. | |
| 2010/0185289 A1 | 7/2010 | Kirwan et al. | |
| 2010/0204737 A1 | 8/2010 | Bae et al. | |
| 2010/0204796 A1 | 8/2010 | Bae et al. | |
| 2010/0217393 A1 | 8/2010 | Theofilos | |
| 2010/0305704 A1 | 12/2010 | Messerli et al. | |
| 2010/0312345 A1 | 12/2010 | Duffield et al. | |
| 2011/0230971 A1 | 9/2011 | Donner et al. | |

FOREIGN PATENT DOCUMENTS

| | | |
|---|---|---|
| WO | 2010054181 A1 | 5/2010 |
| WO | 2011044852 A1 | 4/2011 |

* cited by examiner

BONE STABILIZATION MEMBER WITH BONE SCREW RETENTION MECHANISM

CROSS-REFERENCES TO RELATED APPLICATIONS

The present application is a continuation application of U.S. patent application Ser. No. 13/560,598, filed Jul. 27, 2012, the complete disclosure of which is herein incorporated by reference.

TECHNICAL FIELD

The disclosure is directed to bone stabilization members configured for securement between vertebrae with bone screws and an associated bone screw retention mechanism configured to prevent the bone screws from backing out of the vertebrae. More particularly, the disclosure is directed to a supplemental fixation system for an intervertebral spacer including a bone screw retention mechanism configured to prevent bone screws from backing out of the vertebrae.

BACKGROUND

A variety of devices are known in the art for fixation to the spine in surgical procedures, such as corpectomies and discectomies, for treating spinal conditions in order to alleviate pain or otherwise stabilize the vertebral segment. During a spinal fixation procedure, after removal of a spinal disc and/or vertebra an intervertebral implant may be installed between a first vertebra and a second vertebra to maintain the proper spacing and/or lordosis between the vertebrae and restore stability to the spine. In some instances, the intervertebral implant may be secured to the vertebrae with bone screws. In some instances, an intervertebral spacer may be positioned between the vertebral bodies of the vertebrae and a bone stabilization member, coupled to the intervertebral spacer, may be provided as a supplemental fixation structure to inhibit migration of the intervertebral spacer until bone fusion occurs.

Accordingly, it is desirable to provide alternative bone stabilization constructs, including supplemental fixation structures for intervertebral spacers and other intervertebral implants, to provide stabilization of a spinal segment. Furthermore, it may be desirable to provide a bone screw retention mechanism with the bone stabilization construct to prevent the associated bone screws from postoperatively backing out of the vertebrae.

SUMMARY

The disclosure is directed to several alternative designs, materials and methods of manufacturing medical device structures and assemblies, and uses thereof.

Accordingly, one illustrative embodiment is a bone stabilization construct configured to be secured to a first bony structure and a second bony structure. The bone stabilization construct includes a bone stabilization member and a retention member coupled to the bone stabilization member. The bone stabilization member includes a plurality of bone screw openings, such as a first bone screw opening configured to receive a first bone screw therethrough for securing the bone stabilization member to the first bony structure and a second bone screw opening configured to receive a second bone screw therethrough for securing the bone stabilization member to the second bony structure. In some instances the bone stabilization member may include additional bone screw openings, such as a third bone screw opening configured to receive a third bone screw therethrough for securing the bone stabilization member to the second bony structure. The retention member is configured to be linearly slidable between a first position and a second position while coupled to the bone stabilization member. In the first position, the retention member does not appreciably block any of the first and second bone screw openings thus permitting bone screws to be inserted into the first and second bone screw openings. For example, in some instances the retention member may not extend across any portion of any of the first and second bone screw openings. In the second position the retention member at least partially covers each of the first and second bone screw openings to prevent a bone screw from backing out of the respective bone screw opening. In embodiments including a third bone screw opening, in the first position, the retention member may additionally not appreciably block any of the third bone screw opening thus permitting a bone screw to be inserted into the third bone screw opening. For example, in some instances the retention member may not extend across any portion of any of the first, second and third bone screw openings. In the second position the retention member may at least partially cover each of the first, second and third bone screw openings to prevent a bone screw from backing out of the respective bone screw opening.

Another illustrative embodiment is a spinal implant for positioning between a first vertebra and a second vertebra of a spinal column. The spinal implant includes an intervertebral spacer configured for placement between a vertebral body of the first vertebra and a vertebral body of the second vertebra and a bone stabilization member configured to be coupled to the intervertebral spacer. The bone stabilization member includes a first bone screw opening and a second bone screw opening. The spinal implant also includes a first bone screw extendable through the first bone screw opening to secure the bone stabilization member to the first vertebra and a second bone screw extendable through the second bone screw opening to secure the bone stabilization member to the second vertebra. A retention member is slidably coupled to the bone stabilization member. The retention member is linearly slidable between a first position and a second position while coupled to the bone stabilization member. In the first position the first and second bone screws are permitted to be inserted into the first and second bone screw openings, respectively, and in the second position the retention member prevents the first and second bone screws from being removed from the first and second bone screw openings. In some instances the bone stabilization member may include a third bone screw opening and the spinal implant may include a third bone screw extendable through the second bone screw opening to secure the bone stabilization member to the second vertebra. In the first position the first, second and third bone screws are permitted to be inserted into the first, second and third bone screw openings, respectively, and in the second position the retention member prevents each of the first, second and third bone screws from being removed from the first, second and third bone screw openings.

Yet another illustrative embodiment is a method of retaining a plurality of bone screws to a bone stabilization member. The method includes inserting a first bone screw through a first bone screw opening of a bone stabilization member with a retention member coupled to the bone stabilization member in a first position, inserting a second bone screw through a second bone screw opening of the bone stabilization member with the retention member coupled to the bone stabilization member in the first position, and inserting a third bone screw through a third bone screw opening of the bone stabilization member with the retention member coupled to the bone stabilization member in the first position. Thereafter, the retention member is slid linearly from the first position to a second position while coupled to the bone stabilization member. The retention member is then locked in the second position. The retention member prevents each of the first, second and third bone screws from being removed from the first, second and third bone screw openings, respectively, when locked in the second position.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
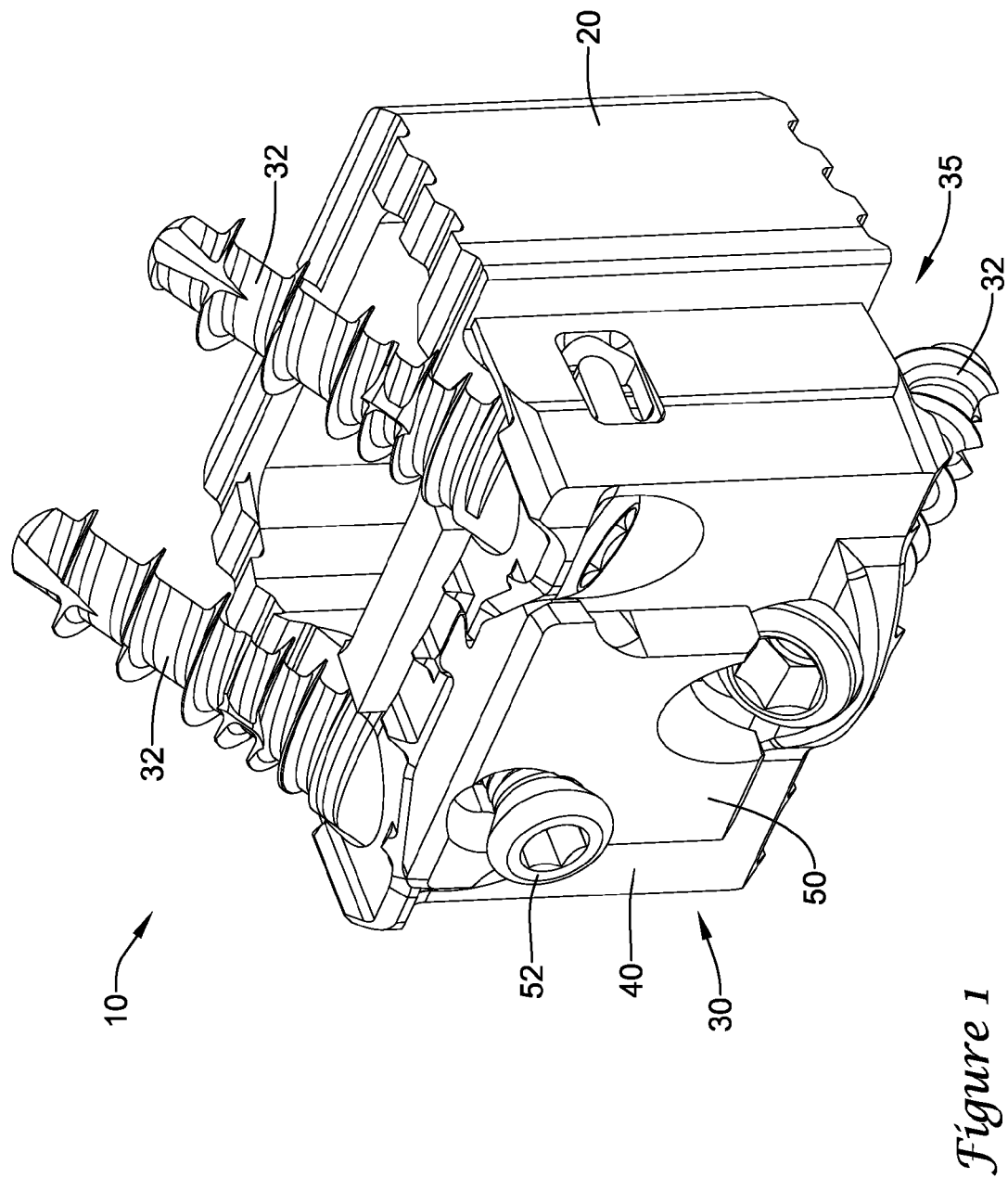
FIG. 1 is a perspective view of an exemplary intervertebral implant including an intervertebral spacer and a supplemental fixation structure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary embodiment of an intervertebral implant 10 including an intervertebral spacer 20 and a supplemental fixation structure 35 is shown in FIG. 1. The intervertebral implant 10 may be configured to be secured between a first vertebra and a second vertebra of a spinal column, such as during a discectomy or corpectomy procedure. For example, one or more, or a plurality of bone screws 32 may be utilized to attach the intervertebral implant 10 to a vertebral body of a superior vertebra and one or more, or a plurality of bone screws 32 may be utilized to attach the intervertebral implant 10 to a vertebral body of an inferior vertebra. It is noted that in the illustrative embodiment the intervertebral implant 10 includes a bone stabilization construct 30 coupled to an intervertebral spacer 20, however, in other embodiments the intervertebral implant 10 may include a bone stabilization construct 30 configured for securing to vertebrae of a spinal column without an intervertebral spacer 20.

Figure 2:
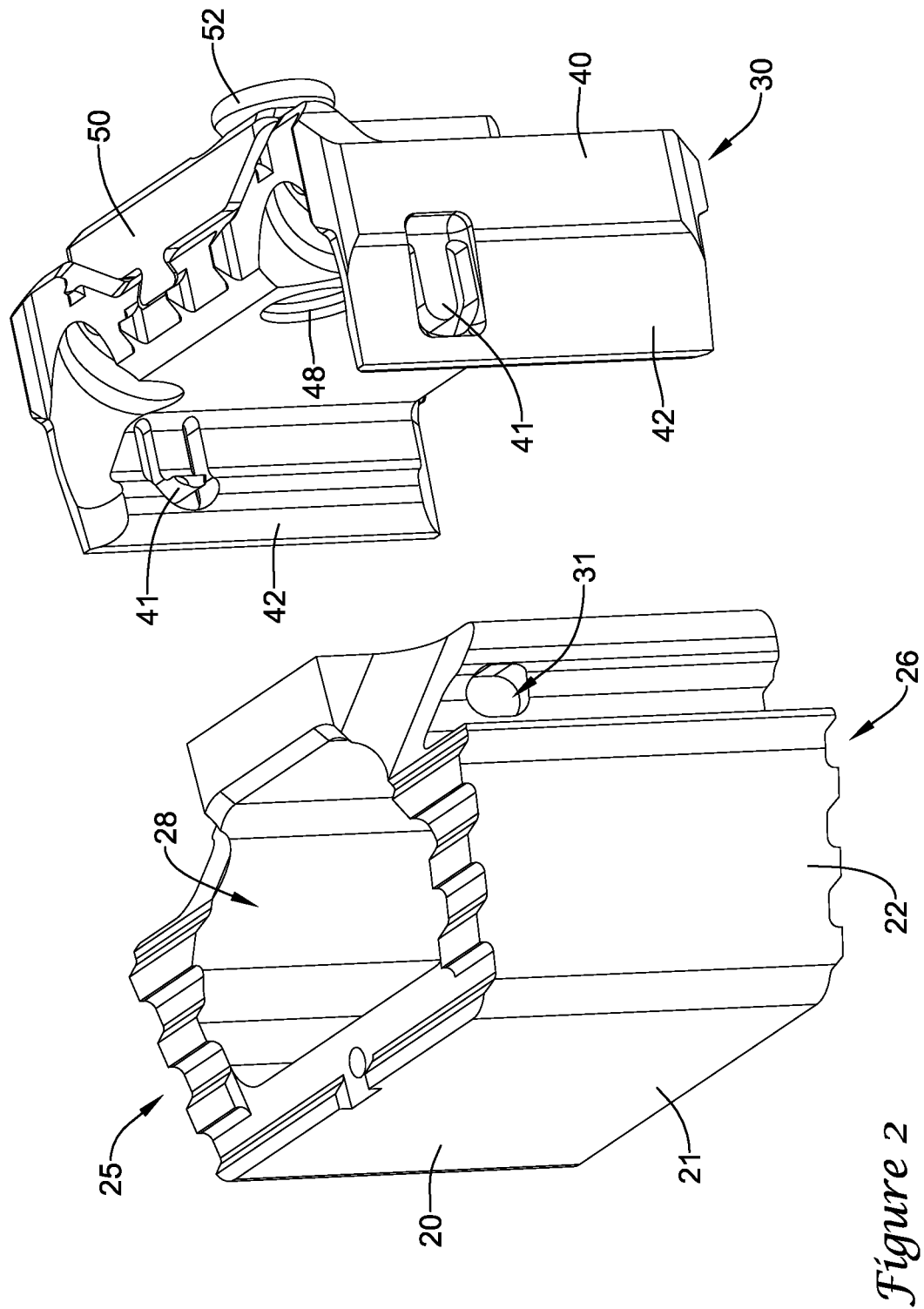
FIG. 2 is an exploded view of the intervertebral spacer and the bone stabilization construct of the intervertebral implant of FIG. 1.
Figure 3:
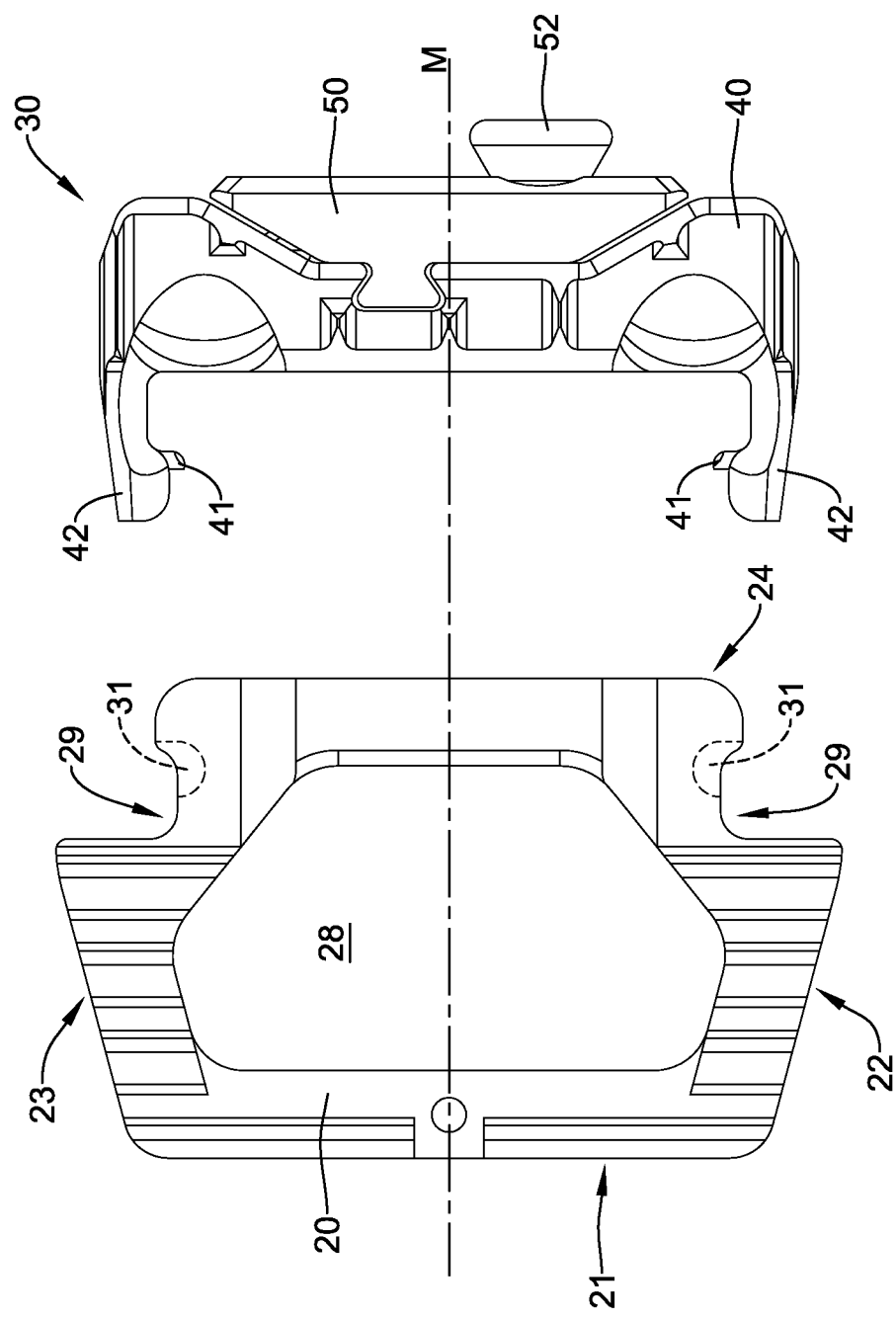
FIG. 3 is a top view of the intervertebral spacer and the bone stabilization construct of the intervertebral implant of FIG. 1.

Turning to FIGS. 2 and 3, the intervertebral spacer 20 may be sized and configured to be positioned between a vertebral body of a superior vertebra and a vertebral body of an inferior vertebra during a discectomy or corpectomy procedure, for example, to maintain proper spacing between the vertebrae. The intervertebral spacer 20 may include a posterior side 21, an anterior side 24 opposite the posterior side 21, lateral sides 22, 23 extending between the posterior side 21 and the anterior side 24, a superior side 25 configured to face or contact an inferior surface of a vertebral body of a superior vertebra, and a opposing inferior side 26 configured to face or contact a superior surface of a vertebral body of an inferior vertebra. The superior and/or inferior sides 25, 26 may include teeth, grooves or other anti-migration structures to engage the vertebral bodies to assist stabilizing the intervertebral spacer 20 between the vertebrae. Additionally, in some instances the intervertebral spacer 20 may include a cavity 28, or a plurality of cavities, which may be filled with bone growth material to facilitate postoperative fusion between the superior and inferior vertebrae.

The intervertebral spacer 20 may be constructed of a polymer material, such as polyetheretherketone (PEEK), a metallic material, such as stainless steel or titanium, or any other suitable biocompatible material, as desired.

The supplemental fixation structure 35, shown as a bone stabilization construct 30 may be coupled or couplable to the intervertebral spacer 20. I some instances, the bone stabilization construct 30 may be a bone plate, or other structure configured to be secured to vertebrae or other bony structures. The bone stabilization construct 30 may include a bone stabilization member 40 and a retention member 50 movably coupled to the bone stabilization member 40. For example, the retention member 50 may be slidably coupled to the bone stabilization member 40 such that the retention member 50 is only permitted to slide in first and second opposite directions within a single plane.

The bone stabilization member 40 and/or the retention member may be constructed of a polymer material, such as polyetheretherketone (PEEK), a metallic material, such as stainless steel or titanium, or any other suitable biocompatible material, as desired.

The bone stabilization construct 30 may be configured to be coupled to the intervertebral spacer 20 by any desired means. For example, the bone stabilization member 40 may include an engagement structure configured to engage or mate with an engagement structure of the intervertebral spacer 20, or a fastener, such as a threaded fastener, may be used to couple the bone stabilization member 40 to the intervertebral spacer 20. In other instances, the bone stabilization member 40 may be integrally coupled to the intervertebral spacer 20 by forming the bone stabilization member 40 and the intervertebral spacer 20 as a unitary structure, and movably coupling the retention member 50 to the bone stabilization member 40 of the unitary structure.

In the illustrative embodiment, the bone stabilization member 40 may be configured to be snap fit to or otherwise interlock with an anterior portion of the intervertebral spacer 20. For example the bone stabilization member 40 may include first and second arms 42 configured to interlock in channels 29 of the intervertebral spacer 20. Furthermore, a tang 41 on each arm 42, which may be flexibly deflected relative to the arm 42, may be configured to engage in opposing openings or notches 31 formed in the intervertebral spacer 20 to further interlock or engage the bone stabilization member 40 with the intervertebral spacer 20. For instance, the tangs 41 may be deflected outward as an anterior portion of the intervertebral spacer 20 is positioned between the arms 42 and then return to or toward an equilibrium position as the tangs 41 engage in the openings or notches 31 of the intervertebral spacer 20.

Figure 4:
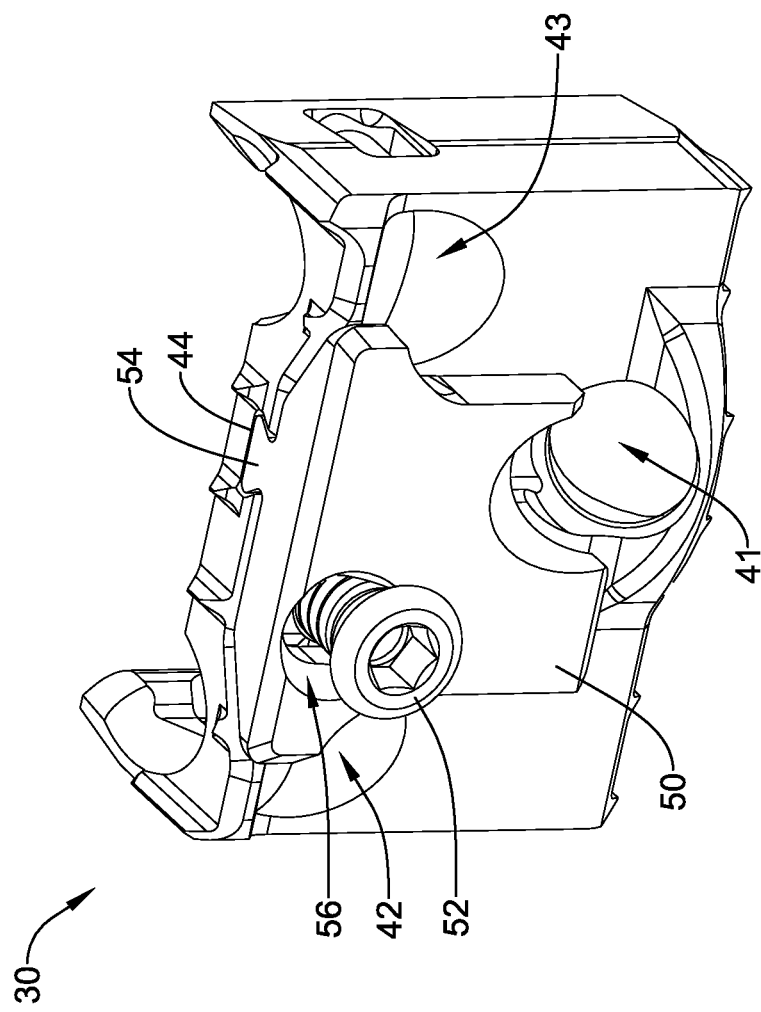
FIG. 4 is a perspective view of the bone stabilization construct of FIG. 1 with the retention member in a first, unlocked position.

As shown in FIG. 4, the bone stabilization member 40 may include a plurality of openings to receive bone screws therethrough to secure the bone stabilization member 40 to vertebrae. For example, the bone stabilization member 40 may include a first bone screw opening 41 configured to receive a first bone screw 32 therethrough to anchor the bone stabilization member 40 to a first bony structure (e.g., a first, inferior vertebra), a second bone screw opening 42 configured to receive a second bone screw 32 therethrough to anchor the bone stabilization member 40 to a second bony structure (e.g., a second, superior vertebra), and a third bone screw opening 43 configured to receive a third bone screw 32 therethrough to anchor the bone stabilization member 40 to the second bony structure (e.g., the second, superior vertebra). The second bone screw opening 42 may be positioned proximate a first lateral edge of the bone stabilization member 40, the third bone screw opening 43 may be positioned proximate an opposite second lateral edge of the bone stabilization member 40, and the first bone screw opening 41 may be positioned at a location intermediate the second bone screw opening 42 and the third bone screw opening 43. The first, second and third bone screw openings 41, 42, 43 may be arranged such that the first bone screw opening 41 is offset from, and not aligned between the second and third bone screw openings 42, 43. In other words, the first bone screw opening 41 may be arranged so that a line extending between the central axes of the second and third bone screw openings 42, 43 does not pass through the central axis of the first bone screw opening 41.

Figure 5:
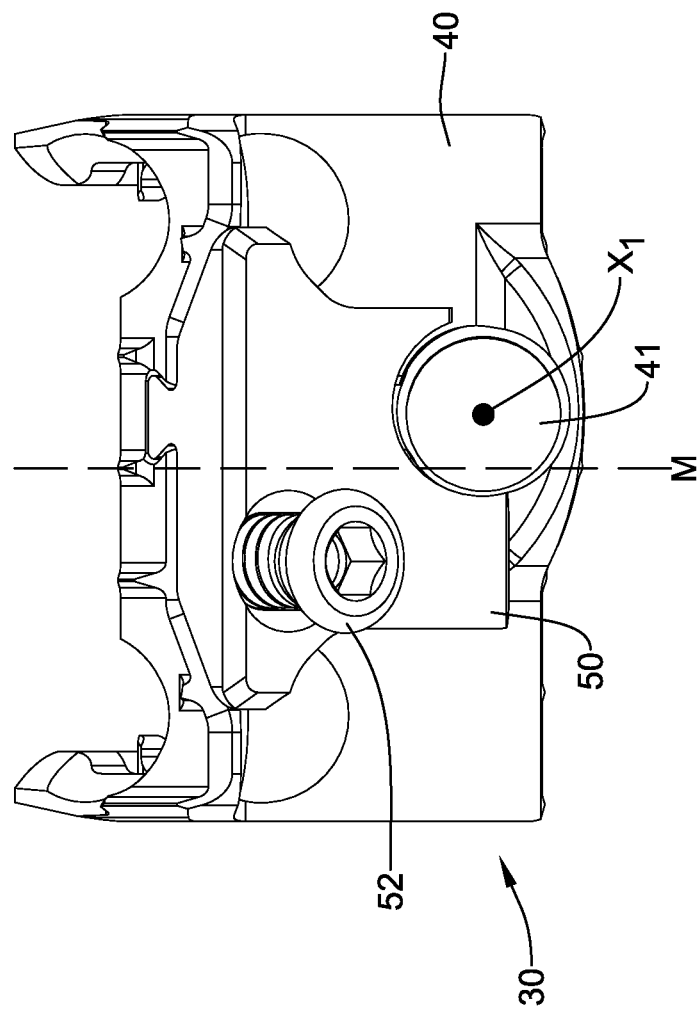
FIG. 5 is a view generally along the central longitudinal axis of a first bone screw opening of the bone stabilization construct, with the retention member in a first, unlocked position.
Figure 6:
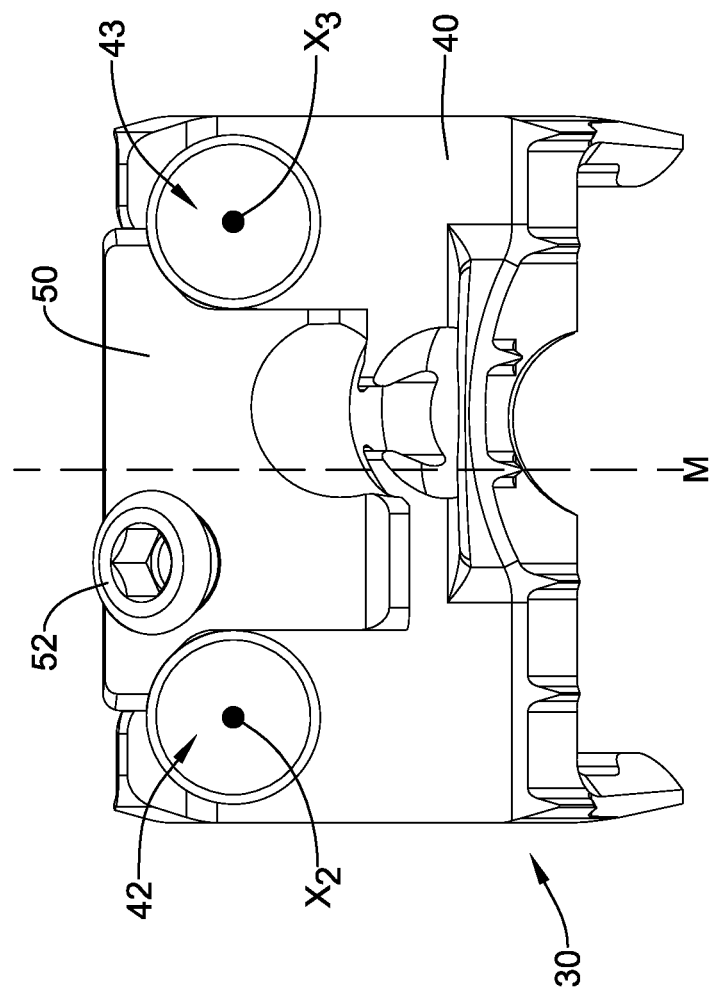
FIG. 6 is a view generally along the central longitudinal axis of second and third bone screw openings of the bone stabilization construct, with the retention member in a first, unlocked position.

Referring to FIGS. 5 and 6, the central axis $X_1$ of the first bone screw opening 41 may be offset from the midplane M of the intervertebral implant 10, and thus the first bone screw opening 41 may be positioned closer to the central axis $X_3$ of the third bone screw opening 43 than to the central axis $X_2$ of the second bone screw opening 42, while the central axes $X_2$, $X_3$ of the second and third bone screw openings 42, 43 may be spaced equidistant from the midplane M on either side of the midplane M. The midplane M is an imaginary plane extending in a superior/inferior direction extending through the middle of the intervertebral implant 10 equidistant between lateral sides of the intervertebral spacer 20. By offsetting the first bone screw opening 41 away from the midplane M, the spacing of the locking screw 52 and the first bone screw opening 41 may be arranged to accommodate a wider range of heights of the bone stabilization member 40, and thus the intervertebral spacer 20, therefore permitting bone stabilization members 40 and intervertebral spacers 20 having a shorter height to be constructed.

The retention member 50 may be configured to be selectively actuatable between a first position (shown in FIGS. 4-6) permitting bone screws 32 to be inserted through the bone screw openings 41, 42, 43 and a second position (shown in FIGS. 7-9) preventing the bone screws 32 from backing out or being removed from the bone screw openings 41, 42, 43 once the bone stabilization member 40 is secured to the bony structures with the bone screws 32. The retention member 50 may be configured to simultaneously cover or be positioned over at least a portion of each of the bone screw openings 41, 42, 43 in the second, locked position, thus preventing each of the bone screws 32 from backing out.

In the illustrative embodiment, the retention member 50 may be slidably coupled to the bone stabilization member 40, permitting linear actuation of the retention member 50 relative to the bone stabilization member 40 along a longitudinal axis to slide the retention member 50 between the first, unlocked position and the second, locked position. Thus, in some embodiments, the retention member 50 may be linearly slidable between the first and second positions without rotational movement of the retention member 50.

A locking screw 52 may be provided to couple the retention member 50 to the bone stabilization member 40. For example, the locking screw 52 may extend through an elongated opening 56 of the retention member 50 and threadably engage a threaded bore 48 of the bone stabilization member 40. In some instances, the locking screw 52 may be prevented from being fully unthreaded from the threaded bore 48 during use, thus insuring that the locking screw 52 will remain with the bone stabilization member 40 while the surgeon is installing the bone stabilization construct 30 to the bony structures. The elongated opening 56 may have a length and a width, with the length being greater than the width. The locking screw 52 may be permitted to travel along the length of the elongated opening 56 as the retention member 50 is moved between the first position and the second position.

The retention member 50 may also include an engagement structure configured to mate with a complementary engagement structure of the bone stabilization member 40. For example, the retention member 50 may include a protrusion 54, such as a dovetail shaped protrusion, sized and configured to mate in a slot or channel 44, such as a dovetail shaped slot or channel, in the bone stabilization member 40. The protrusion 54 may be configured to slide along the longitudinal axis of the channel 44 as the retention member 50 is linearly actuated between the first and second positions, without permitting the protrusion 54 from being uncoupled from the channel 44. In other embodiments, the protrusion 54 may be T-shaped to mate with a T-shaped channel, or otherwise shaped to prohibit the protrusion 54 from being removed from the channel 54 in a direction perpendicular to the longitudinal axis of the channel 44 as the retention member 50 is linearly moved between the first and second positions. Engagement of the protrusion 54 within the channel 44 may permit the retention member 50 to move in first and second opposite directions relative to the bone stabilization member 40 along the longitudinal axis of the channel 44, while prohibiting movement of the retention member 50 relative to the bone stabilization member 40 in all other directions. The protrusion 54 and the channel 44 may be constructed such that the protrusion 54 is at least partially positioned in the channel 44 along the full length of travel of the locking screw 52 in the elongated opening 56 of the retention member 50. Additionally, engagement of the protrusion 54 within the channel 44 may retain the retention member 50 in a desired orientation relative to the bone stabilization member 40, as well as provide strength and/or stability to the portion of the retention member 50 located above the first bone screw opening 41 and extending toward the third bone screw opening 43.

The elongated opening 56 may be configured such that as the locking screw 52 is tightened (e.g., rotation of the locking screw 52 causing the head of the locking screw 52 to bear against the retention member 50), the head of the locking screw 52 engages the rim of the elongated opening 56. For example, the locking screw 52 may include a driver interface, such as a hex opening or other standard driver interface (or a specialized driver interface, if desired) to engage with a driver, such as a hex wrench or other standard driver (or a specialized driver) to tighten the locking screw 52. In some instances, it may be desirable to provide a locking screw 52 having a standard driver interface, such as a hex opening, to facilitate subsequent loosening of the locking screw 52 during a revision surgery at a later date, where the medical personnel performing the revision surgery may not have a specialized driver, but would have access to standardized drivers fitting the driver interface of the locking screw 52.

As the locking screw 52 is tightened, the head of the locking screw 52 may interact with the rim of the elongate opening 56 such that when the head of the locking screw 52 is pressed against the rim, forces generated between the head of the locking screw 52 and the retention member 50 cause the retention member 50 to move toward the second position. The rim of the elongate opening 56 may include a seating portion (visible in FIG. 4) in which the head of the locking screw 52 is seated when the retention member 50 is in the second position. Thus, as the locking screw 52 is tightened, the head of the locking screw 52 moves toward and into the seating portion of the elongated opening 56. Upon sufficient tightening of the locking screw 52, the retention member 50 may be firmly secured to the bone stabilization member 40 such that no further movement of the retention member 50 is permitted.

FIG. 5 illustrates a view of the bone stabilization construct 30 generally along the central longitudinal axis $X_1$ of the first bone screw opening 41 of the bone stabilization construct 30, with the retention member 50 in the first, unlocked position. FIG. 6 illustrates a view of the bone stabilization construct 30 generally along the central longitudinal axes $X_2$, $X_3$ of the second and third bone screw openings 42, 43 of the bone stabilization construct 30, with the retention member 50 in the first, unlocked position. In the first position, the retention member 50 may be loosely coupled to the bone stabilization member 40 with the locking screw 52 and the protrusion 54 in the channel 44. For example, the retention member 50 may be moved into the first position by raising the retention member 50 toward the upper side of the bone stabilization member 40, and thus toward the superior side 25 of the intervertebral spacer 20, such that the loosened locking screw 52 is moved into a lower portion of the elongated opening 56. In the first position the first, second and third bone screws 32 may be permitted to be inserted into the first, second and third bone screw openings 41, 42, 43, respectively, without being inhibited by the retention member 50. For example, in the first position, the retention member 50 may be clear of and not cover or extend across any portion of any of the first, second and third bone screw openings 41, 42, 43 or otherwise may not substantially block any of the first, second and third bone screw openings 41, 42, 43, and thus permit the first, second and third bone screws 32 to be inserted into the first, second and third bone screw openings 41, 42, 43, respectively. In other words, in some instances, in the first position all portions of the retention member 50 may be located radially outward of and not impede into the diameter of any of the first, second and third bone screw openings 41, 42, 43, for example.

Figure 7:
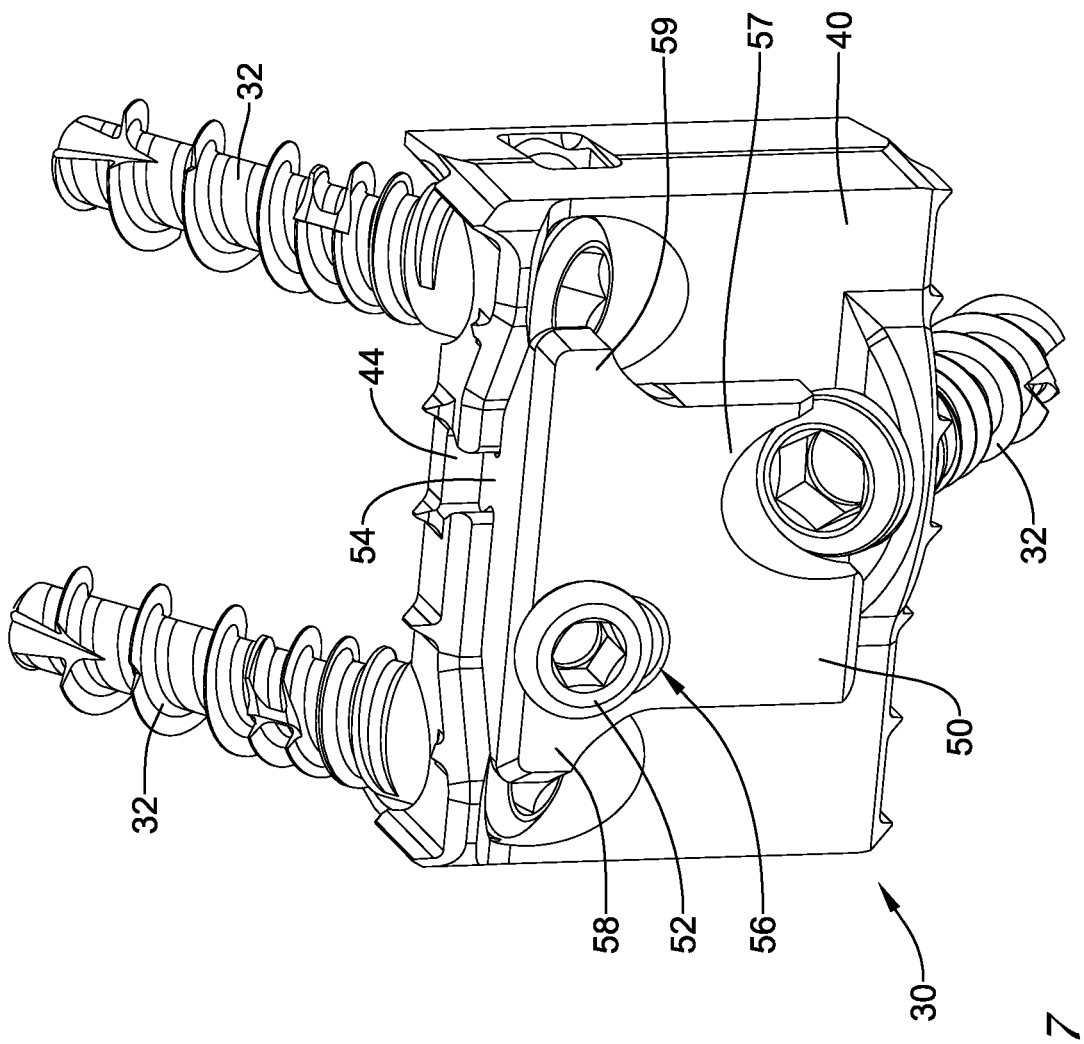
FIG. 7 is a perspective view of the bone stabilization construct of FIG. 1 with the retention member in a second, locked position.

FIG. 7 illustrates the bone stabilization construct 30 with the retention member 50 moved downward to the second position upon tightening the locking screw 52. As the retention member 50 is moved toward the second position, the locking screw 52 may travel in the elongated opening 56 toward the seating portion of the elongated opening 56 at the upper extent of the elongated opening 56. In the second position, portions of the retention member 50 may cover or extend across portions of each of the first, second and third bone screw openings 41, 42, 43 and thus the heads of respective bone screws 32 extending therethrough to prevent the bone screws 32 from backing out of the bone screw openings 41, 42, 43. For example, in the second position the retention member 50 may include a first portion, such as an arcuate edge 57 defining an arcuate cutout portion of the retention member 50 at least partially covering the first bone screw opening 41 (and associated bone screw 32), a second portion, such as a first tab 58, at least partially covering the second bone screw opening 42 (and associated bone screw 32), and a third portion, such as a second tab 59, at least partially covering the third bone screw opening 43 (and associated bone screw 32).

Figure 8:
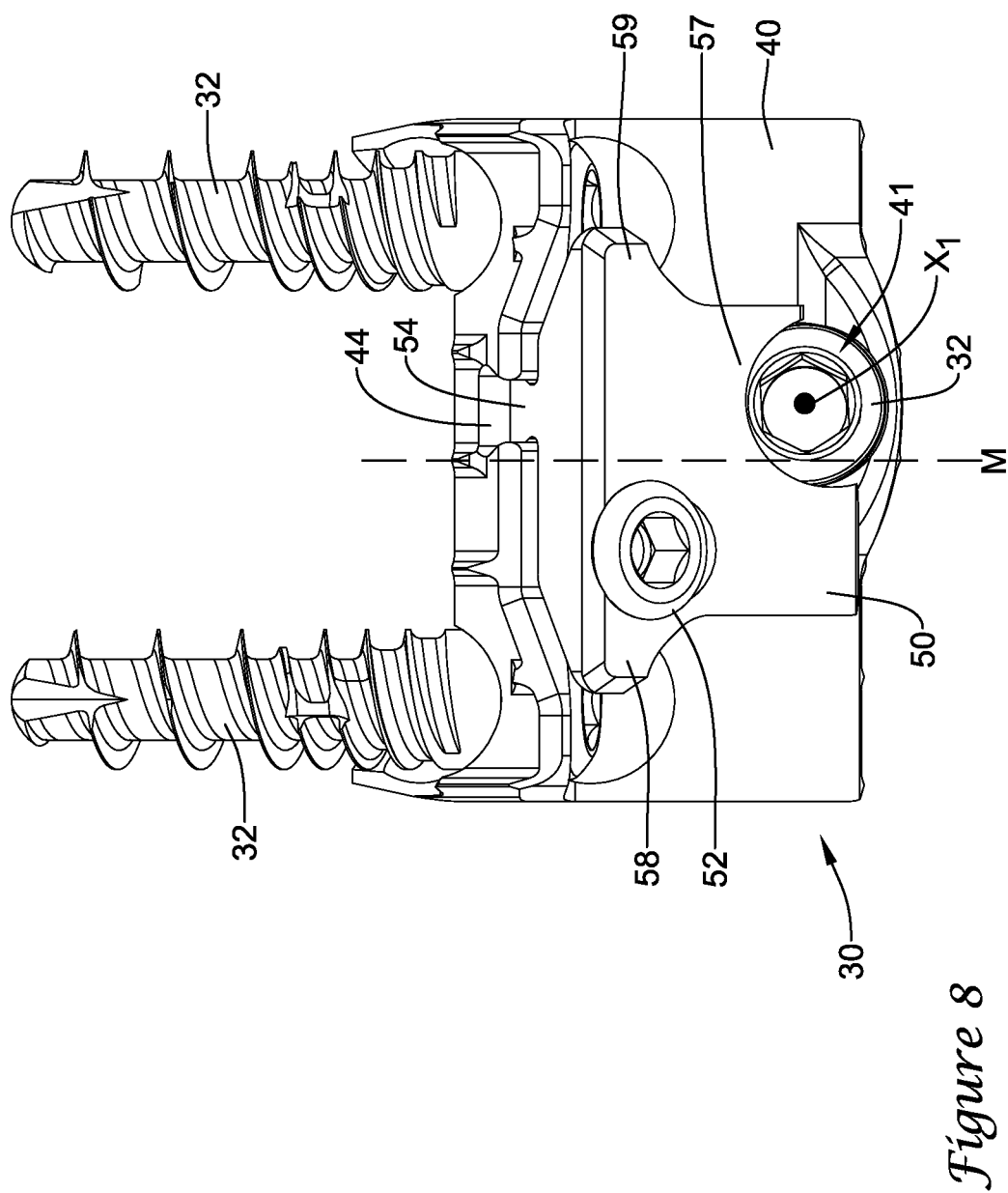
FIG. 8 is a view generally along the central longitudinal axis of a first bone screw opening of the bone stabilization construct, with the retention member in a second, locked position.
Figure 9:
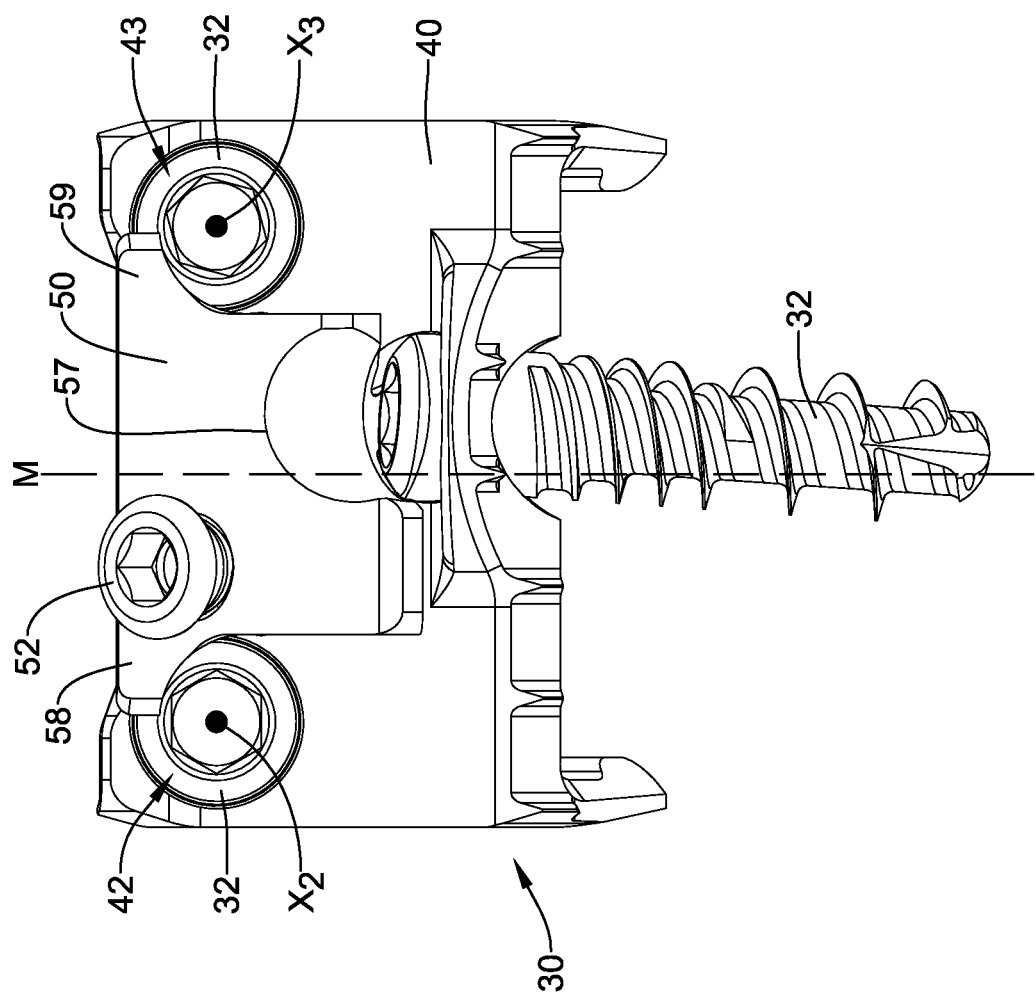
FIG. 9 is a view generally along the central longitudinal axis of second and third bone screw openings of the bone stabilization construct, with the retention member in a second, locked position.

FIG. 8 illustrates a view of the bone stabilization construct 30 generally along the central longitudinal axis $X_1$ of the first bone screw opening 41 of the bone stabilization construct 30, with the retention member 50 in the second, locked position. FIG. 9 illustrates a view of the bone stabilization construct 30 generally along the central longitudinal axes $X_2$, $X_3$ of the second and third bone screw openings 42, 43 of the bone stabilization construct 30, with the retention member 50 in the second, locked position. In the second position, the retention member 50, fixedly secured to the bone stabilization member 40 via tightening the locking screw 52, may at least partially cover each of the first, second and third bone screw openings 41, 42, 43 to prevent a bone screw 32 from backing out of the respective bone screw opening. In other words, in the second position a portion of the retention member 50 may be located radially inward of and impede into the diameter of each of the first, second and third bone screw openings 41, 42, 43.

Figure 10:
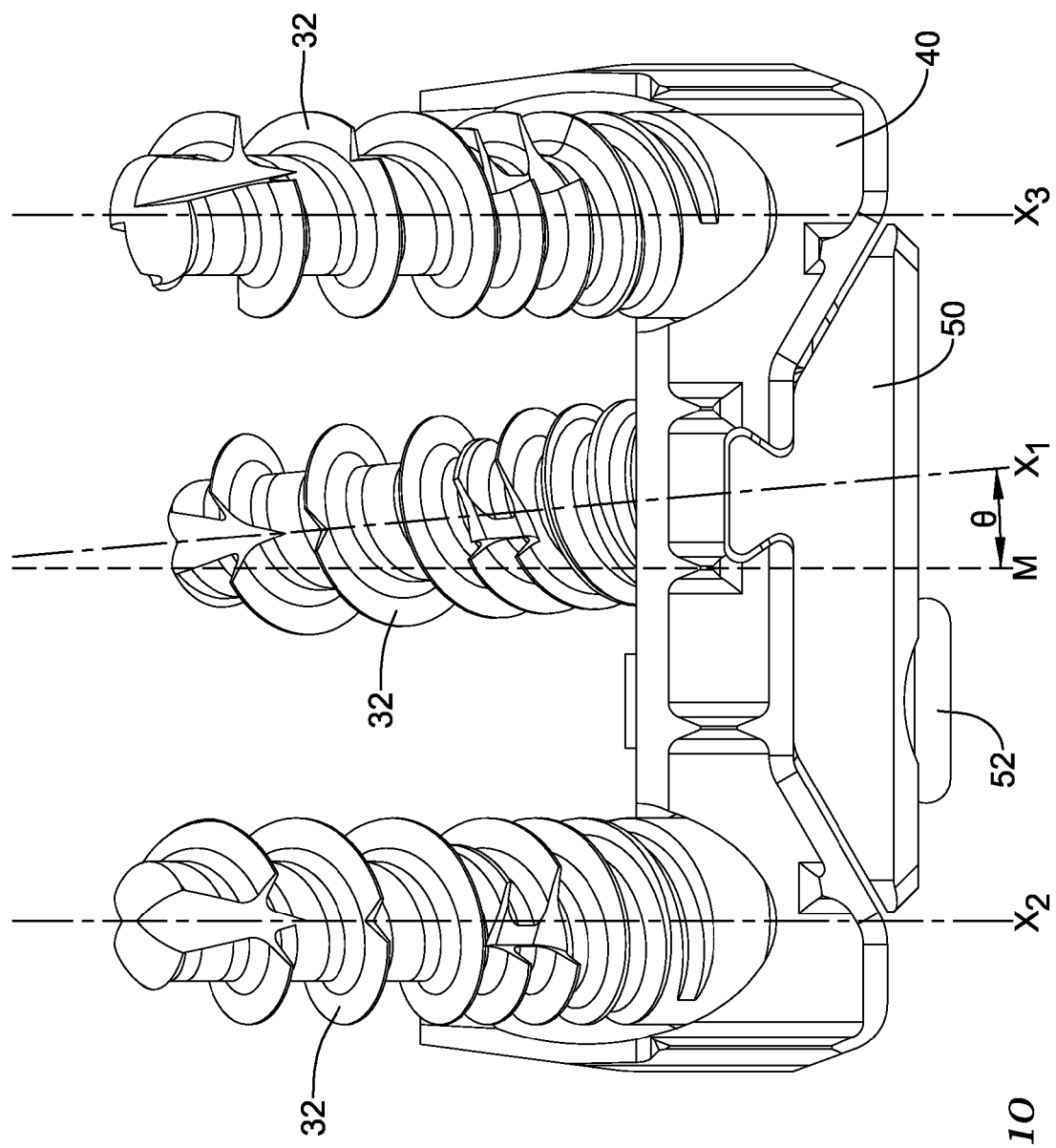
FIG. 10 is a top view of the bone stabilization construct with bone screws extending through the bone screw openings.

As shown in FIG. 10, the second and third bone screw openings 42, 43 may be configured such that the central axis of the associated bone screws 32 extend along the central axis of the second and third bone screw openings 42, 43 generally parallel to the midplane M of the intervertebral implant 10. Since the first bone screw opening 41 is offset from the midplane M, the first bone screw opening 41 may be configured to angle the distal tip of the bone screw 32 extending therethrough toward the midplane M from the first bone screw opening 41. For example, the first bone screw opening 41 may be configured such that the central axis of the first bone screw 32, which may be coaxial with the central axis $X_1$ of the first bone screw opening 41, may be at an angle θ to the midplane M. For example, the central axis of the first bone screw 32 may extend at an angle θ in the range of about 1 to 10 degrees, for example, about 1, about 2, about 3, about 4, about 5, about 6, about 7, about 8, about 9 or about 10 degrees from the midplane M, if desired, in order to angle the distal tip of the bone screw 32 toward the midplane M.

Figure 11:
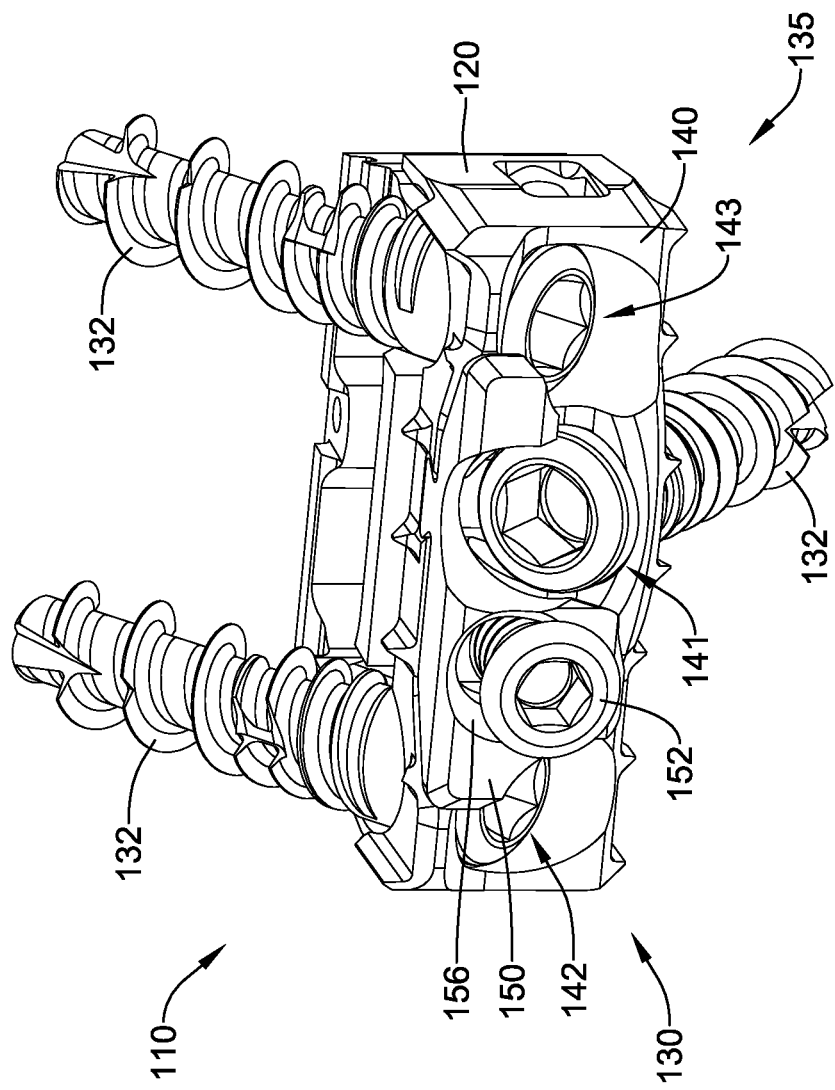
FIG. 11 is a perspective view of another exemplary intervertebral implant including an intervertebral spacer and a supplemental fixation structure.

Another illustrative embodiment of an intervertebral implant 110 is shown in FIG. 11. The intervertebral implant 110 may share many similarities to the intervertebral implant 10. For example, the intervertebral implant 110 may include an intervertebral spacer 120 and a supplemental fixation structure 135 to facilitate securement of the intervertebral implant 110 between a first vertebra and a second vertebra of a spinal column. For example, one or more, or a plurality of bone screws 132 may be utilized to attach the intervertebral implant 110 to a vertebral body of a superior vertebra and one or more, or a plurality of bone screws 132 may be utilized to attach the intervertebral implant 110 to a vertebral body of an inferior vertebra.

The supplemental fixation structure 135, shown as a bone stabilization construct 130 may be coupled or couplable to the intervertebral spacer 120. The bone stabilization construct 130 may include a bone stabilization member 140 and a retention member 150 movably coupled to the bone stabilization member 140. For example, the retention member 150 may be slidably coupled to the bone stabilization member 140 such that the retention member 150 is only permitted to slide linearly in first and second opposite directions within a single plane.

A locking screw 152 may be provided to couple the retention member 150 to the bone stabilization member 140. For example, the locking screw 152 may extend through an elongated opening 156 of the retention member 150 and threadably engage a threaded bore of the bone stabilization member 140. As the locking screw 152 is tightened, the head of the locking screw 152 may interact with the rim of the elongate opening 156 such that when the head of the locking screw 152 is pressed against the rim, forces generated between the head of the locking screw 152 and the retention member 150 cause the retention member 150 to move from the first, unlocked position toward the second, locked position to prevent the bone screws 132 from backing out.

FIG. 11 illustrates a configuration of an intervertebral implant 110 having a height less than the height of the intervertebral implant 10 shown in FIG. 1. As shown in FIG. 11, offsetting the first bone screw opening 141 from the midplane M of the intervertebral implant 110 to a first side of the midplane M, while offsetting the locking screw 152 and associated elongated opening 156 to a second side of the midplane M opposite the first bone screw opening 141, may permit the construction of intervertebral implants having a smaller height dimension than the combined heights of the elongated opening 156 and the first bone screw opening 141. Accordingly, a set of intervertebral implants having a range of heights may be provided during a surgical procedure, including heights less than the combined heights of the elongated opening 156 and the first bone screw opening 141 without reducing the size of the locking screw 152 and/or the bone screws 132.

Figure 12:
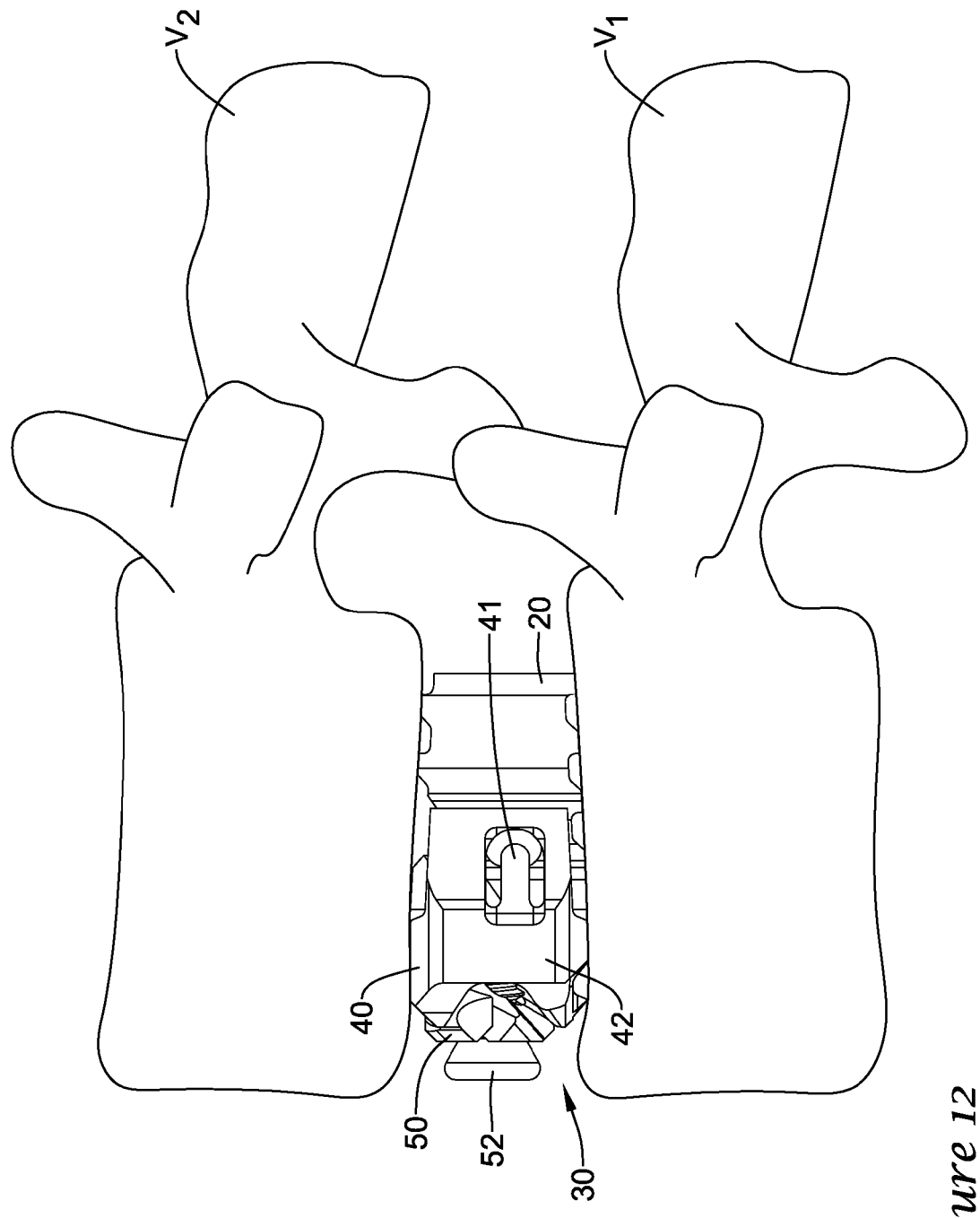
FIGS. 12-14 illustrate an illustrative method of installing the intervertebral implant to first and second vertebrae of a spinal column.
Figure 13:
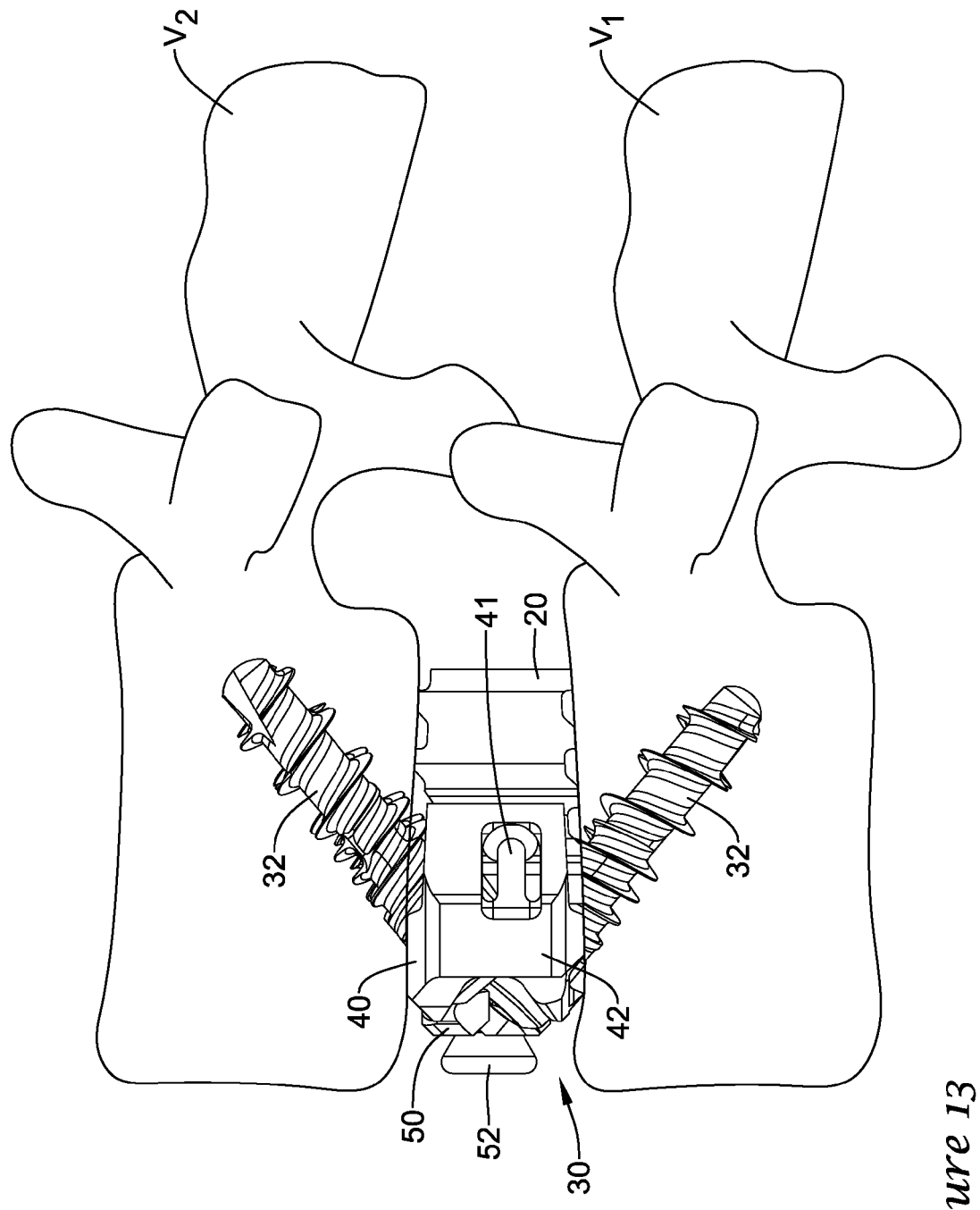
Figure 14:
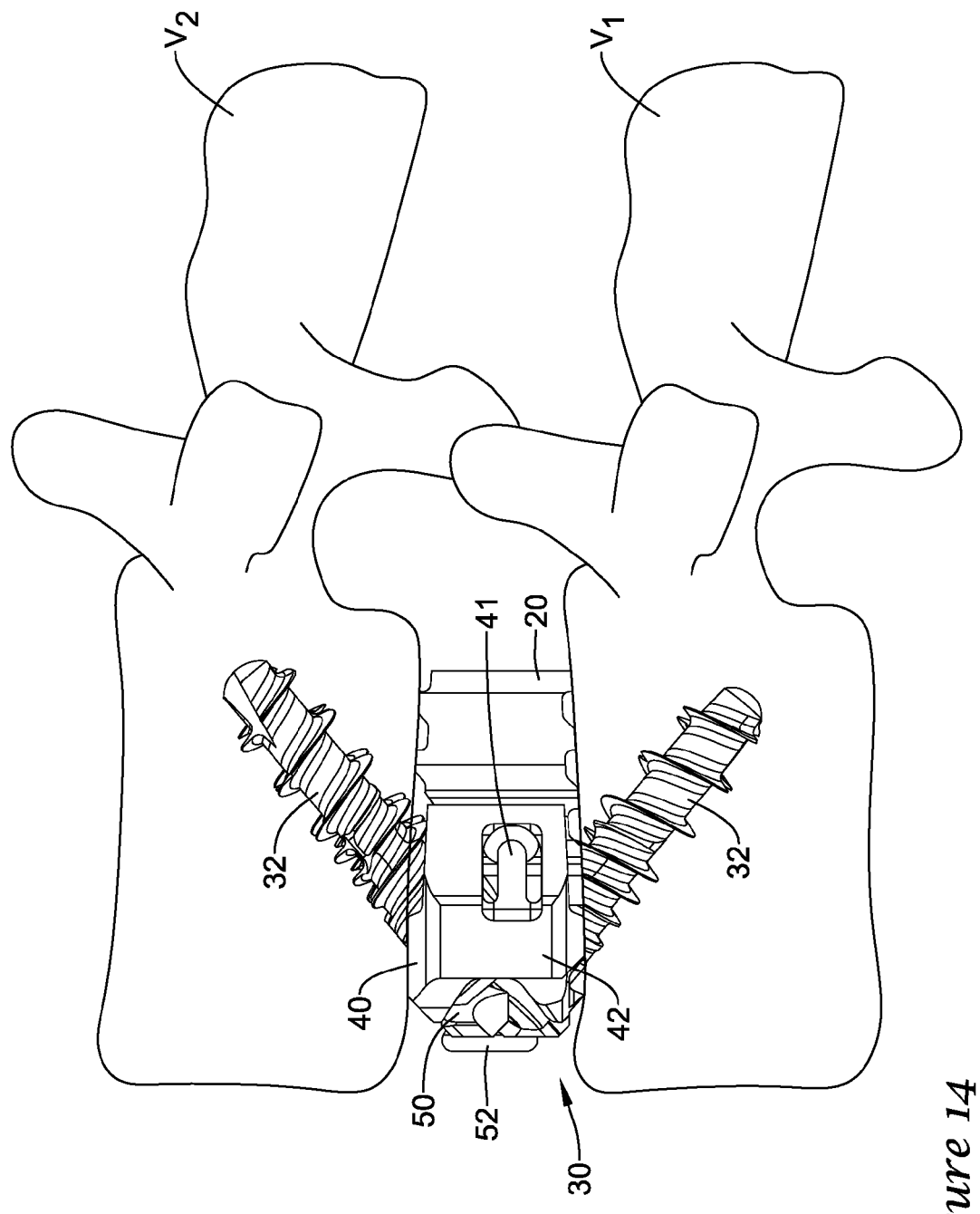

FIGS. 12-14 illustrate one exemplary method of installing the intervertebral implant 10 to first and second vertebrae $V_1$, $V_2$ of a spinal column. The intervertebral implant 10 may maintain the proper spacing and/or lordosis between the vertebrae $V_1$, $V_2$ and restore stability to the spine.

n some instances, the intervertebral implant 10 may be provided with the bone stabilization construct 30 coupled to the intervertebral spacer 20. If not already coupled to the intervertebral spacer 20, the bone stabilization construct 30 may be intraoperatively coupled to the intervertebral spacer 20 prior to installing the intervertebral implant 10. It is noted that in some instances, the bone stabilization construct 30 may be coupled to or otherwise interlocked with the intervertebral spacer 20 subsequent to installing the intervertebral spacer 20 between the vertebrae $V_1$, $V_2$, if desired. The bone stabilization construct 30 may be coupled to the anterior portion of the intervertebral spacer 20. For example, the bone stabilization member 40 may be snap coupled to the intervertebral spacer 20 such that the first and second arms 42 of the bone stabilization member 40 are positioned on either side of the anterior portion and the tangs 41 are engaged in the openings or notches 31 of the intervertebral spacer 20.

As shown in FIG. 12, after preparing a space between the vertebral bodies of the vertebrae $V_1$, $V_2$, such as during a discectomy or corpectomy procedure, the intervertebral spacer 20 and the bone stabilization construct 30 of the intervertebral implant 10 may be inserted between the vertebral body of the first vertebra $V_1$ and the vertebral body of the second vertebra $V_2$ using an insertion instrument (not shown). For instance, the intervertebral implant 10, including the intervertebral spacer 20 and/or the bone stabilization construct 30, may be inserted using an anterior approach, in which the posterior side of the intervertebral spacer 20, which may be considered the leading side, is inserted first and directed posteriorly into the space between the vertebrae $V_1$, $V_2$, from the anterior side of the spinal column.

The inferior surface of the intervertebral spacer 20 may be configured to engage a superior surface of the vertebral body of the first vertebra $V_1$ and the superior surface of the intervertebral spacer 20 may be configured to engage an inferior surface of the vertebral body of the second vertebra $V_2$. In some instances, the superior and inferior surfaces may be generally parallel, disposed at an angle, or have a curvature to accommodate the proper spacing and/or lordosis between the vertebrae $V_1$, $V_2$. If desired, the cavity 28 may be filled with bone growth material prior to inserting the intervertebral spacer 20 to promote subsequent fusion between the vertebrae $V_1$, $V_2$.

Thereafter, as shown in FIG. 13, bone screws 32 may be inserted through the bone screw openings 41, 42, 43 of the bone stabilization member 40 and screwed into the vertebrae $V_1$, $V_2$ while the retention member 50 is in the first, unlocked position. For instance, a first bone screw 32 may be inserted through the first bone screw opening 41 of the bone stabilization member 40 with the retention member 50 coupled to the bone stabilization member 40 in the first position. The first bone screw 32 may be screwed into the vertebral body of the first vertebra $V_1$ to anchor the bone stabilization member 40 to the first vertebra $V_1$. A second bone screw 32 may be inserted through the second bone screw opening 42 of the bone stabilization member 40 and a third bone screw 32 may be inserted through the third bone screw opening 43 with the retention member 50 coupled to the bone stabilization member 40 in the first position. The second and third bone screws 32 may be screwed into the vertebral body of the second vertebra $V_2$ to anchor the bone stabilization member 40 to the second vertebra $V_2$.

Thereafter, the retention member 50 may be moved to the second position to extend across at least a portion of each of the first, second and third bone screw openings 41, 42, 43 to prevent the bone screws 32 from backing out of the bones. For example, as shown in FIG. 14, the retention member 50 may be slid linearly relative to the bone stabilization member 40 from the first position to the second position while coupled to the bone stabilization member 40, and thereafter locked in the second position. For example, the locking screw 52 may be tightened (e.g. rotated with a driver). By rotating the locking screw 52 threadably coupled to the bone stabilization member 40, the locking screw 52 may exert a force on the rim of the elongated opening 56 of the retention member 50 to slide the retention member 50 linearly from the first position to the second position. The protrusion 54 may follow along the channel 44 of the bone stabilization member 40 as the retention member 50 moves toward the second position. The locking screw 52 may be rotated until the locking screw 52 has traveled along the length of the elongated opening 56 a sufficient distance such that the head of the locking screw 52 is seated in the seating portion of the elongate opening 56. Sufficient torque may be applied to the locking screw 52 to securely seat the head of the locking screw 52 in the seating portion and secure the retention member 50 from further movement relative to the bone stabilization member 40. When locked in the second position, the retention member 50 may prevent each of the first, second and third bone screws 32 from being removed from the first, second and third bone screw openings 41, 42, 43, respectively.

It is noted that in other embodiments, the bone stabilization construct 30, 130 may be used in other applications, such as trauma to secure two bony structures (e.g. two bony portions of a single bone, or a first bone and a second bone) with a plurality of bone screws 32, 132. In some such applications, it is noted that the bone stabilization construct 30, 130 may be used without the intervertebral spacer 20, 120. In some instances, the bone stabilization member 30, 130 may be secured to two bony structures with a first bone screw 32, 132 screwed into a first bony structure and second and third bone screws 32, 132 screwed into a second bony structure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A spinal implant for positioning between a first vertebra and a second vertebra, the spinal implant comprising:
an intervertebral spacer configured for placement between a vertebral body of the first vertebra and a vertebral body of the second vertebra;
a bone stabilization member configured to be coupled to the intervertebral spacer;
the bone stabilization member including a first bone screw opening, a second bone screw opening, and a third bone screw opening;
a first bone screw extendable through the first bone screw opening to secure the bone stabilization member to the first vertebra;
a second bone screw extendable through the second bone screw opening to secure the bone stabilization member to the second vertebra;
a third bone screw extendable through the third bone screw opening to secure the bone stabilization member to the second vertebra;
a retention member coupled to the bone stabilization member, the retention member linearly slidable between a first position and a second position while coupled to the bone stabilization member; and
a locking screw coupling the retention member to the bone stabilization member;
wherein in the first position the first, second and third bone screws are permitted to be inserted into the first, second and third bone screw openings, respectively, and in the second position the retention member prevents the first, second and third bone screws from being removed from the first, second and third bone screw openings.

2. The spinal implant of claim 1, wherein the retention member includes a protrusion slidably engaged in a slot of the bone stabilization member.

3. The spinal implant of claim 1, wherein the locking screw extends through an elongate opening of the retention member into a threaded bore of the bone stabilization member, the elongate opening having a length greater than a width of the elongate opening;
wherein the locking screw travels along the length of the elongate opening as the locking screw is rotated into the threaded bore to move the retention member from the first position to the second position.

4. The spinal implant of claim 1, wherein the intervertebral spacer has a midplane extending in a superior/inferior direction between lateral sides of the intervertebral spacer;
wherein the first bone screw opening is located between the second bone screw opening and the third bone screw opening;
wherein the first bone screw opening is offset to a first side of the midplane; and
wherein the locking screw is offset to a second side of the midplane opposite the first side.

5. The spinal implant of claim 1, wherein the first bone screw opening is located between the second bone screw opening and the third bone screw opening;
wherein the intervertebral spacer has a midplane extending in a superior/inferior direction between lateral sides of the intervertebral spacer;
wherein the first bone screw opening is offset to one side of the midplane; and
wherein the first bone screw angles toward the midplane when extended through the first bone screw opening.

6. The spinal implant of claim 1, wherein the retention member includes a first tab configured to at least partially cover the second bone screw opening in the second position and a second tab configured to at least partially cover the third bone screw opening in the second position.

7. The spinal implant of claim 6, wherein the retention member includes an arcuate edge defining an arcuate cutout portion of the retention member configured to at least partially cover the first bone screw opening in the second position.

8. A spinal implant for positioning between a first vertebra and a second vertebra, the spinal implant comprising:
- an intervertebral spacer configured for placement between a vertebral body of the first vertebra and a vertebral body of the second vertebra;
- a bone stabilization member configured to be coupled to the intervertebral spacer; the bone stabilization member including a first bone screw opening, a second bone screw opening, and a third bone screw opening;
- a first bone screw extendable through the first bone screw opening to secure the bone stabilization member to the first vertebra;
- a second bone screw extendable through the second bone screw opening to secure the bone stabilization member to the second vertebra;
- a third bone screw extendable through the third bone screw opening to secure the bone stabilization member to the second vertebra;
- a retention member coupled to the bone stabilization member, the retention member movable between a first position and a second position while coupled to the bone stabilization member; and
- a locking screw coupling the retention member to the bone stabilization member, wherein rotation of the locking screw about a rotational axis causes the retention member to move in a direction generally perpendicular to the rotational axis;
- wherein the first bone screw opening is located between the second bone screw opening and the third bone screw opening;
- wherein the intervertebral spacer has a midplane extending in a superior/inferior direction between lateral sides of the intervertebral spacer;
- wherein the first bone screw opening is offset to one side of the midplane; and
- wherein the first bone screw angles toward the midplane when extended through the first bone screw opening.

9. The spinal implant of claim 8, wherein in the second position the retention member prevents at least one of the first, second and third bone screws from being removed from bone stabilization member.

10. The spinal implant of claim 8, wherein rotation of the locking screw causes the locking screw to travel along an elongate opening of the retention member.

11. The spinal implant of claim 10, wherein the locking screw interacts with a rim of the elongate opening such that when a head of the locking screw is pressed against the rim the retention member moves toward the second position.

12. The spinal implant of claim 8, wherein the retention member includes a protrusion slidably disposed in a slot of the bone stabilization member.

13. The spinal implant of claim 12, wherein the protrusion is dovetail shaped and the slot is dovetail shaped to mate with the dovetail shape of the protrusion.

14. The spinal implant of claim 8, wherein the retention member is configured to simultaneously cover at least a portion of each of the first, second and third bone screw openings.

* * * * *